(12) United States Patent
Bobrowski

(10) Patent No.: US 7,632,524 B2
(45) Date of Patent: *Dec. 15, 2009

(54) PHARMACEUTICAL PREPARATIONS FOR THE TREATMENT OF ITCH, NAUSEA, HYPERALGESIA AND THE COMPLICATIONS OF OPIOID AGONISTS

(76) Inventor: Paul J. Bobrowski, 5030 E. Libby St., Scottsdale, AZ (US) 85254

( * ) Notice: Subject to any disclaimer, the term of this patent is extended or adjusted under 35 U.S.C. 154(b) by 1035 days.

This patent is subject to a terminal disclaimer.

(21) Appl. No.: 10/679,006

(22) Filed: Oct. 4, 2003

(65) Prior Publication Data

US 2004/0067270 A1 Apr. 8, 2004

Related U.S. Application Data

(60) Provisional application No. 60/416,750, filed on Oct. 5, 2002.

(51) Int. Cl.
*A01N 65/00* (2006.01)
(52) U.S. Cl. ............................................ 424/725
(58) Field of Classification Search .................. 424/725
See application file for complete search history.

(56) References Cited

U.S. PATENT DOCUMENTS 3,809,749 A * 5/1974 Persinos .................... 424/771
5,264,638 A * 11/1993 Nilubol ...................... 568/875
5,958,437 A * 9/1999 Zaveri ........................ 424/401
2002/0155073 A1 * 10/2002 Fankhauser et al. ......... 424/59

FOREIGN PATENT DOCUMENTS

| EP | 000897712 | * | 2/1999 |
|---|---|---|---|
| JP | 52070010 | * | 6/1977 |
| JP | 52144665 | * | 12/1977 |
| JP | S52-144665 | * | 12/1977 |
| JP | 07010777 | * | 1/1995 |
| JP | 10-231239 | * | 9/1998 |
| JP | 410231239 | * | 9/1998 |
| JP | 411139952 | * | 5/1999 |
| JP | H11-139952 | * | 5/1999 |
| JP | 12-336024 | * | 12/2000 |
| JP | 2000336024 | * | 12/2000 |

* cited by examiner

*Primary Examiner*—Michael V Meller
(74) *Attorney, Agent, or Firm*—Venable, Campillo, Logan & Meaney P.C.

(57) ABSTRACT

The invention herein describes an improved and novel means of managing the complications of opioid analgesics, specifically treating the induction of emesis and itch by suppressing the activation of sensory afferent nerves. The composition of the botanical components that provides these benefits do not sacrifice hyperalgesia in order to negate the activity of sensory afferent nerves that drive emesis and itch, but in contrast affords significant analgesic actions in its own right. The combination of a therapeutic approach that negates an increased sensitivity to pain, itch, and nausea is a significant improvement over current treatment options.

4 Claims, 7 Drawing Sheets

PHARMACEUTICAL PREPARATIONS FOR THE TREATMENT OF ITCH, NAUSEA, HYPERALGESIA AND THE COMPLICATIONS OF OPIOID AGONISTS

This application claims benefit of U.S. Provisional Application Ser. No. 60/416,750 filed on Oct. 5, 2002.

BACKGROUND OF THE INVENTION

1. Field of the Invention

The present invention is relevant to the field of suppressing sensory afferent neuron mediated symptoms and the manufacture of agents and compositions which suppress the same.

2. Discussion of the Related Art.

Sensory afferent nerves mediate a number of symptoms that affect the quality of life. Specifically, itch, pain, nausea, cough, diarrhea, motion sickness, vomiting and retching, in addition to sensations of touch, heat and cold.

Often these troubling symptoms become severe enough to warrant therapeutic intervention. However, current therapeutic options to achieve a broad array of benefits are extremely limited. Only recently has our understanding advanced to the point that we now recognize that these symptoms are mediated by subsets of sensory afferent nerves, largely on the basis of pharmacological studies defining agonist response relationships and direct electrochemical measurement of nerve conduction.

What are also lacking are therapeutic options that suppress the heightened nerve activity in various pathological states. It is also now recognized that subset of nerves mediating certain responses can affect the detection of related symptoms also mediated by sensory afferent nerves. The classic example of this is the ability of opioid narcotics to block pain but yet stimulate the sensations of itch and nausea. Conversely, activation of pain fibers with capsaicin has been used as a treatment for refractory itch. From this it is clear that an agent that was a broad inhibitor of sensory afferent nerve activation would possess therapeutic advantages over current approaches by providing more generalized relief in response to a range of provocative events, as well as by not exchanging one symptom for another.

Sangre de grado, the viscous latex derived from various Croton species plants found primarily in the Amazon River basin, is an effective agent in managing a range of symptoms and complications mediated by activation of sensory afferent nerves. Sangre de grado or extracts derived thereof, can block the hyperalgesia, hyperemia, edema promoting, secretory actions associated with capsaicin stimulation. However, by blocking pain pathways Sangre de grado does not establish an itch response, but conversely it also blocks itch.

In response to insect bites, stings and plant reactions where a host of skin responses occur—itch, pain, edema, redness, discomfort, Sangre de grado extracts are effective in rapidly blocking the range of symptoms as opposed to a selective sensory response.

SUMMARY OF THE INVENTION

Aspects of the invention are summarized below to aid in the understanding of embodiment(s) of the invention and the application. Yet, the invention is fully defined by the claims of the application.

Sensory afferent nerves mediate a number of symptoms that can adversely affect the quality of life. However, current therapeutic approaches either limit applications to individual symptoms or may offer relief of certain symptoms by enhancing the sensitivity to other annoying symptoms.

For these reasons, management of these quality of life conditions is inadequate. The current embodiment describes the use of an ethnomedicine, the latex of Croton species, used by indigenous peoples of the Amazon to provide broad relief of itch, pain, nausea, and cough. However, the ethnomedicine has undesirable properties that limit its use.

The present invention generally comprises methods and compositions for topical and oral use, with an improved safety profile, and markedly reduced color so as to afford applications to skin without discoloration or staining of clothing. The methods and compositions described herein contain botanical derivatives that retain the ability to inhibit the perioperative effects of opioid narcotics specifically, emesis and itch, as well as providing inherent analgesic properties an suppression of neurogenic inflammation.

The composition is further incorporated into biologically active dosing units forming beneficial compositions, which address nausea, itch, emesis, hyperalgesia, motion sickness and opioid agonist-induced complications.

BRIEF DESCRIPTION OF THE FIGURES

FIG. 2. Prevention of opioid-induced itch by Zangrado. Itch, as measured by the number of licking episodes per hour, was induced by parenteral administration of the opioid narcotic, morphine-6-glucuronide (15 mg/kg) ip. Administration of Zangrado (3 mg/kg) 15 minutes prior to morphine blocked this response (P<0.01), and this protection was not reversed by the cannabinoid antagonist AM 251 indicating that the benefits observed with Zangrado were not mediated by activation of cannabinoid receptors. Note: AM251 promotes licking in naïve animals, reflecting the ant pruritic effects of endogenous cannabinoids.

DESCRIPTIONS OF EMBODIMENTS

Figure 1:
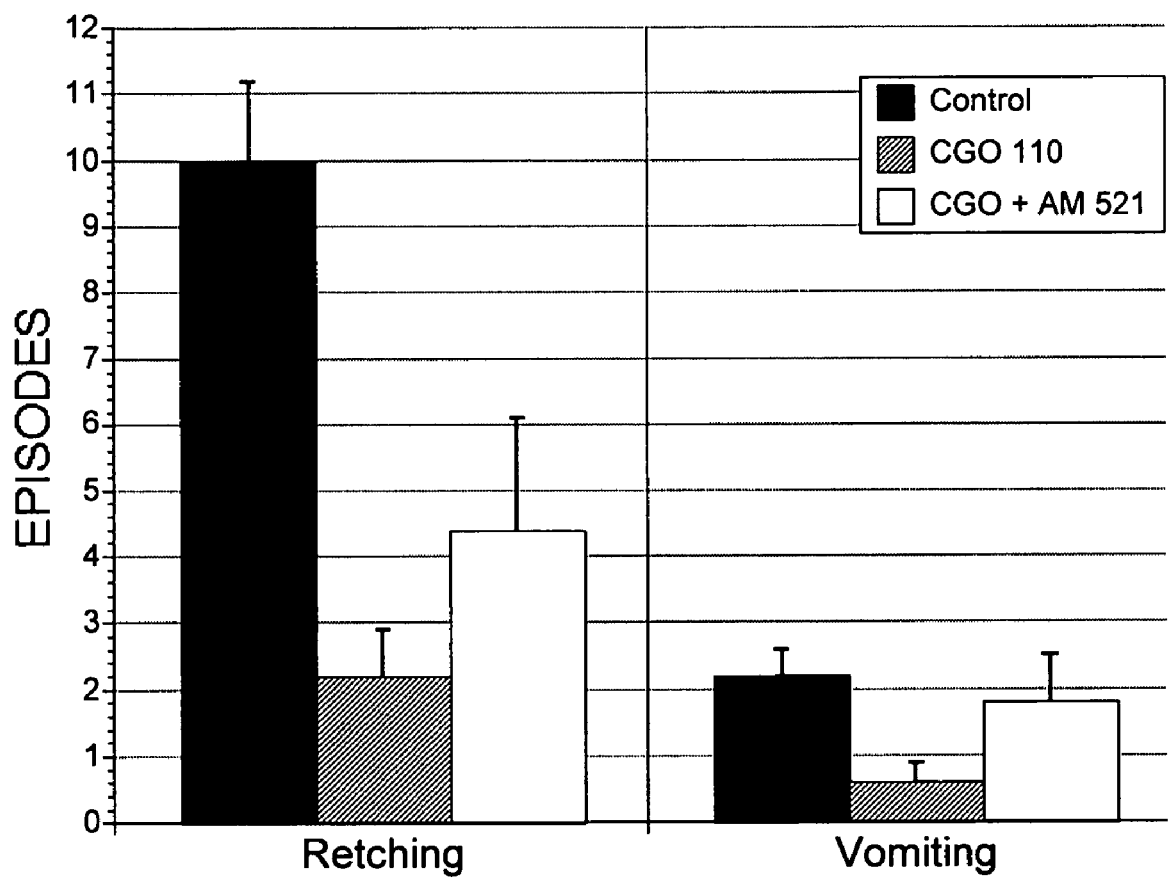
FIG. 1. Prevention of opioid-induced emesis by the Croton speceis extract, (Zangrado®). Emesis as measured by the number of vomiting and retching episodes per hour was induced by parenteral administration of the opioid narcotic, morphine-6-glucuronide (15 mg/kg) ip. Administration of Zangrado (3 mg/kg) 15 minutes prior to morphine blocked this response (P<0.01), and this protection was not reversed by the cannabinoid antagonist AM 251 indicating that the benefits observed with Zangrado were not mediated by activation of cannabinoid receptors. Note: AM251 promotes emesis in naïve animals, reflecting the ant emetic effects of endogenous cannabinoids.

Aspects of the invention are summarized below to aid in the understanding of embodiment(s) of the invention and the application. Yet, the invention is fully defined by the claims of the application.

Extraction Procedure

According to one aspect of this invention, a process that retains and concentrates the lipophilic components while reducing the hydrophilic proanthocyanidin content of the plant material resolves a family Euphorbaciae extraction. This extraction process significantly reduces the extracted composition of the hydrophilic proanthocyandins, and hence its intense burgundy color, making it more amenable to topical health care preparations. Furthermore, the product of this lipidic extraction, Zangrado (CGO 110), is selectively cytotoxic to cancerous cells, unlike the parent material, representing an improvement in safety and suggesting applications in the treatment of cancerous cells. Preferred methods to accomplish the aforementioned family Euphorbaciae extraction are described by the procedures below but it is contemplated that a skilled practitioner could device obvious variations of the procedures given the disclosure herein and the desired results.

Extraction Process 1.

Latex, or sap from *Croton* species is mixed with an organic solvent. The preferred organic solvent is ethyl acetate although other organic solvents can be used as would be obvious to the ordinarily skilled practitioner in light of the disclosure herein. In other embodiments, the preferred organic solvent is isopropanol, a chloroform/Methanol mixture, or an equivalent thereof. The organic solvent is added to the latex in a 1:1 proportion. In the preferred extraction process the solvent latex combination is agitated.

The preferred agitation method is stirring although other agitation methods are also contemplated to be effective. Following agitation, the mixture is settled, or allowed to settle into distinct phases including at least an organic layer and an aqueous layer. The organic phase or layer is comprised largely of solute lipophilic materials, representing the active constituent, and a significantly reduced quantity of proanthocyanidin components relative to the pre-agitation step. The organic layer is separated from the aqueous layer for further processing pursuant to the preferred extraction process.

Moreover, it is common to find a gel-like substance in the organic layer at the interface of the aqueous and organic layers. This gel substance is characterized as having a dark brown and purple color and comprises hydrophilic constituents trapped with water. In the preferred process the gel substance is processed further to separate any active lipophilic constituents from the hydrophilic constituents. The preferred manner of processing the gel substance is the addition of a drying agent to the organic layer or the gel substance. The preferred drying agent is magnesium sulfate in a concentration of 0.5-5 g/L of contaminant gel. It is contemplated that other equivalent drying agents at relative effective concentrations would also be effective and would be obvious to the ordinarily skilled practitioner in light of the disclosure herein and with undue experimentation.

The addition of the drying agent results in a precipitant, which traps water and hydrophilic constituents or water-based colored chemical contaminants. The precipitant can be readily separated from the hydrophilic constituents by filtration or other techniques known to separate precipitants. Actual laboratory procedures achieved acceptable results using a Whatman #4 filter paper or an equivalent.

The steps of organic extraction, mixing with a drying agent and filtration may be repeated up to three times to accomplish a thorough extraction of the active lipophilic constituents. At this point in the process, the lipophilic materials are solutes contained within the organic solvent, which are concentrated by evaporation of the solvent by one of several procedures, such as vacuum drying, freeze drying or heating. Actual heating up to 60 degrees Celsius produced acceptable drying results.

The organic layer composition thus processed is rich in lipophilic materials but largely clear of hydrophilic contaminants. Following the extraction process, the color of the organic layer can be characterized as a rose. Moreover, the reduced proanthocyanidin content is quantifiable spectrophotometrically. Relative absorbance of the extraction in the visible spectrum was compared to the absorbency peak of the parent latex (414 nm) in the visible range.

At a concentration of 1 mg of extracted latex to 1 mL of water the disclosed process yielding the extraction (CGO 110) results in a 4.3 fold reduction in absorbance at 414 nm, as indicated in FIG. 1. This assessment was repeated 9 times with similar results achieved (significance difference $P<0.0001$, as denoted by the "*"). Similarly when Sangre de grado or the extraction (CGO 110) at a concentrations of 200 µg per mL of aloe vera gel were applied to aloe vera gel to mimic their administration as topical products, there was also a significantly lower color response with the extracted Sangre de grado, CGO 110 vs. the parent botanical (* $P<0.0001$). See FIG. 1. Estimates from the absorbency measurements indicate that the proanthocyanidin content was reduced by at least 90% relative to the non-extracted parent latex.

Extraction Process 2.

The latex from the *Croton* species is dried to its residual solid matter by methods such as heating, air-drying, vacuum or freeze-drying. The dried latex is rich in proanthocyanidin compounds and therefore characterized by a dark burgundy color. To the dried latex matter the organic solvent, ethyl acetate or an equivalent, is added. The dried latex and organic solvent mixture is agitated and the organic solvent is removed for further processing according to the procedure described in Example 1. This process may be repeated up to three times to accomplish a thorough extraction all lipophilic materials in the organic layer and solvent. If any water bearing contaminants are present, the addition of drying agent followed by filtration as noted above, will remove these contaminants. Removing the ethyl acetate through various methods including heating, air-drying, vacuum or freeze-drying then isolates the solutes contained within this organic extract.

The extraction thus processed according to the disclosed processes is characterized by a significant reduction of proanthocyanidin compounds. The reduction of the proanthocyanidin compounds leaves the extraction significantly diminished in color producing compounds and yet amenable to health care applications.

A pharmaceutical dosage comprising a biologically active amount of the *Croton* extract produced as taught herein is contemplated for use singularly or in combination with other ingredients for human and animal use. Moreover particularly, a pharmaceutical dosage comprising a biologically active amount of the *Croton* extract can be embodied in suppositories, oral, topical, injectable or inhalable formats.

The pharmaceutical dosage comprising a biologically active amount of the *Croton* extract is administered in a quantity sufficient to ameliorate conditions mediated by sensory afferent nerves, The conditions are contemplated to include, but are not limited to pain, itch, cough, diarrhea nausea, motion sickness, vomiting, retching hyperalgesia and the complications of opioid agonists.

Prevention of Opiod-Induced Emesis

Sangre de Grado has also been used ethnomedically for the treatment of a variety of intestinal complications including diarrhea, ulcerations, cancer and emesis. Using a well-established ferret model of post-operative complications of emesis induced by morphine, Zangrado (CGO 110) was administered intraperitoneally (3 mg/kg) to ferrets 15 minutes prior to the administration of morphine-6-glucuronide (M6G), known to promote itching, retching and vomiting. The animals were monitored for sixty minutes.

As shown in FIG. 1 the subcutaneous injection of 0.05 mg/kg M6G caused a significant number of vomiting (2.2±0.4) and retching (10±1.2) incidences in the control group. In those animals treated with Zangrado (CGO 110), the number of these episodes was virtually abolished (vomiting 0.6±0.3; retching 2.2±0.7, P<0.05). Given the utility of this model to predict treatments for nausea and vomiting, Zangrado (CGO 110) contains active components and is effective in the treatment of emesis.

Prevention of Opiod-Induced Itch

Figure 2:
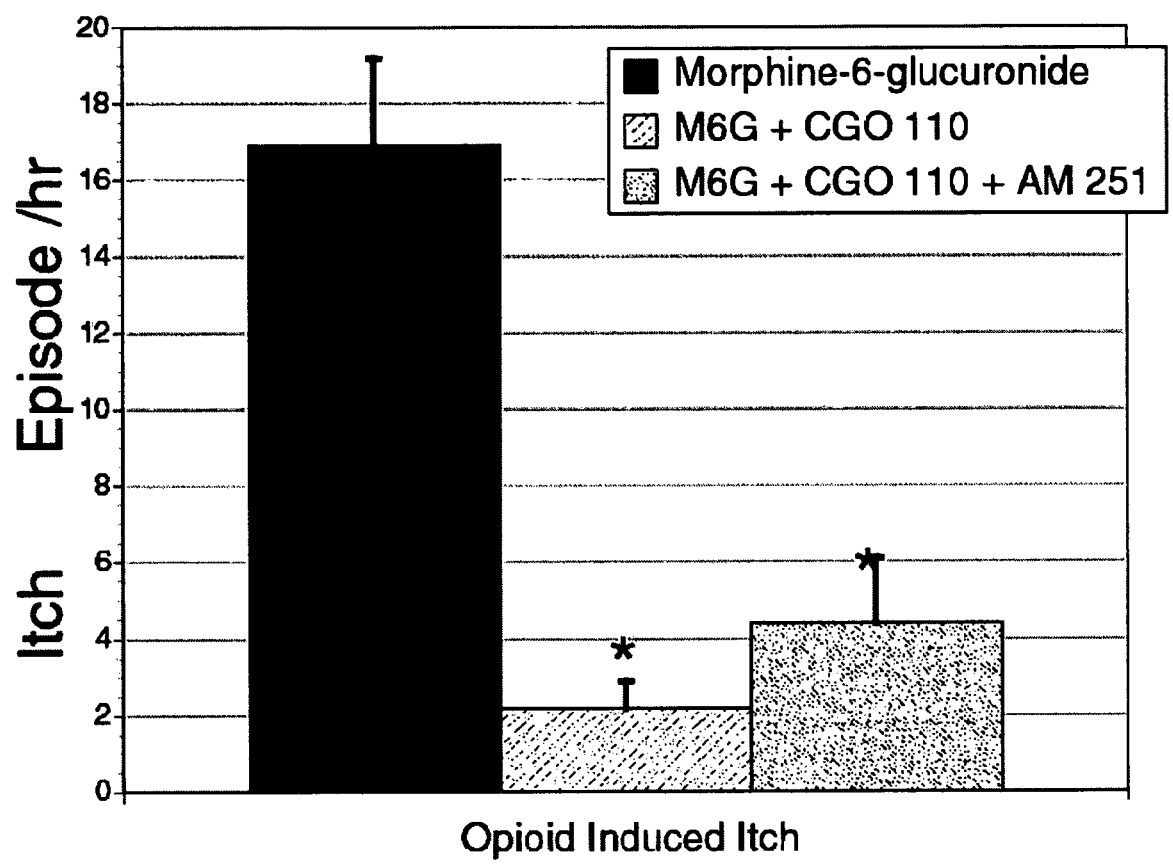
FIG. 2.

In a similar ferret model of post-operative complications induced by the opioid narcotic morphine-6-glucuroniude, as shown in FIG. 2, itch as indicated by licking responses was reduced from a control value of 16.9±2.3 episodes to 2.2±0.7 in Zangrado (CGO 110) treated animals (P0.05). Administration of Zangrado (3 mg/kg) 15 minutes prior to the opioid blocked this response (P<0.01), and this protection was not reversed by the cannabinoid antagonist AM 251 indicating that the benefits observed with Zangrado were not mediated by activation of cannabinoid receptors. Zangrado (CGO 110) contains active components and is effective in the treatment of itch.

Effects on Sensory Afferent Nerve Induced Hyperemia

A prototypical activator of sensory afferent nerves, the nerves that mediate the sensations of pain, itch, cough and nausea is capsaicin, the pungent chemical found in chili peppers. Activation of these nerves by an activator such as capsaicin leads to a multitude of responses including vasodilation (mediated by the release of neurotransmitters from these activated nerves that cause blood vessels to relax), inflammatory cell recruitment, edema, and the sensations of pain and itching. Zangrado (CGO 110) was tested to determine its ability to suppress sensory afferent nerve activation by testing its ability to inhibit capsaicin-induced increases in gastric blood flow.

Figure 3:
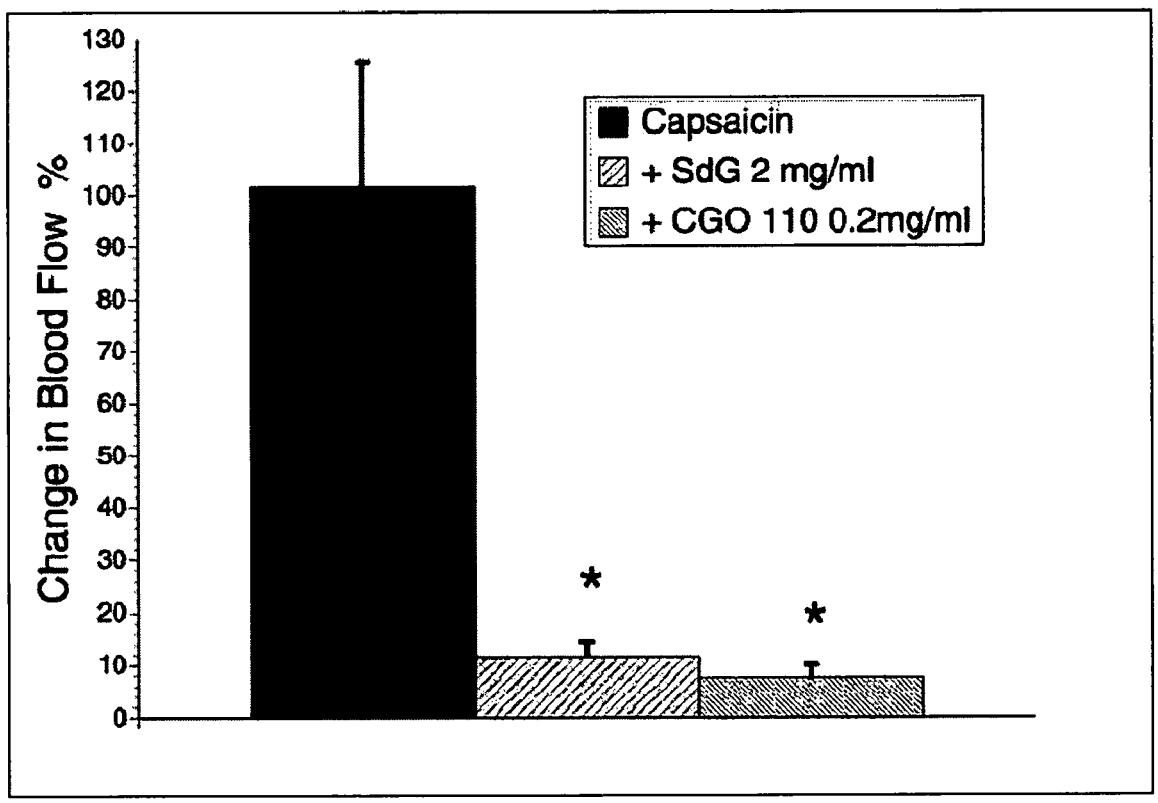
FIG. 3: The prototypical activator of sensory afferent nerves, capsaicin, was topically applied to the mucosal surface of the stomach in anesthetized rats and mucosal blood flow measured by a Laser Doppler Flow meter. The marked increase in mucosal blood flow induced by 300 µM capsaicin was prevented by either the parent material, Sangre de grado or its extract, Zangrado (CGO 110) at doses of 2 and 0.2 mg/ml, respectively, indicating that the organic extract retains the ability to effectively prevent the activation of sensory afferent nerves.

The experiment involved the topical application of capsaicin to the mucosal surface of the stomach in anesthetized rats and mucosal blood flow measured by a laser Doppler flow meter. As indicated in FIG. 3, the marked increase in mucosal blood flow induced by 300 $\mu$M capsaicin was prevented by either the parent material, Sangre de grado (SdG), or its organic extract, Zangrado (CGO 110) deplete of proanthocyanidins at doses of 2 and 0.2 mg/ml, respectively. Thus, the organic extract described in this application (Zangrado) retains the ability to effectively prevent the activation of sensory afferent nerves.

Effects on Hyperalgesia

Figure 4:
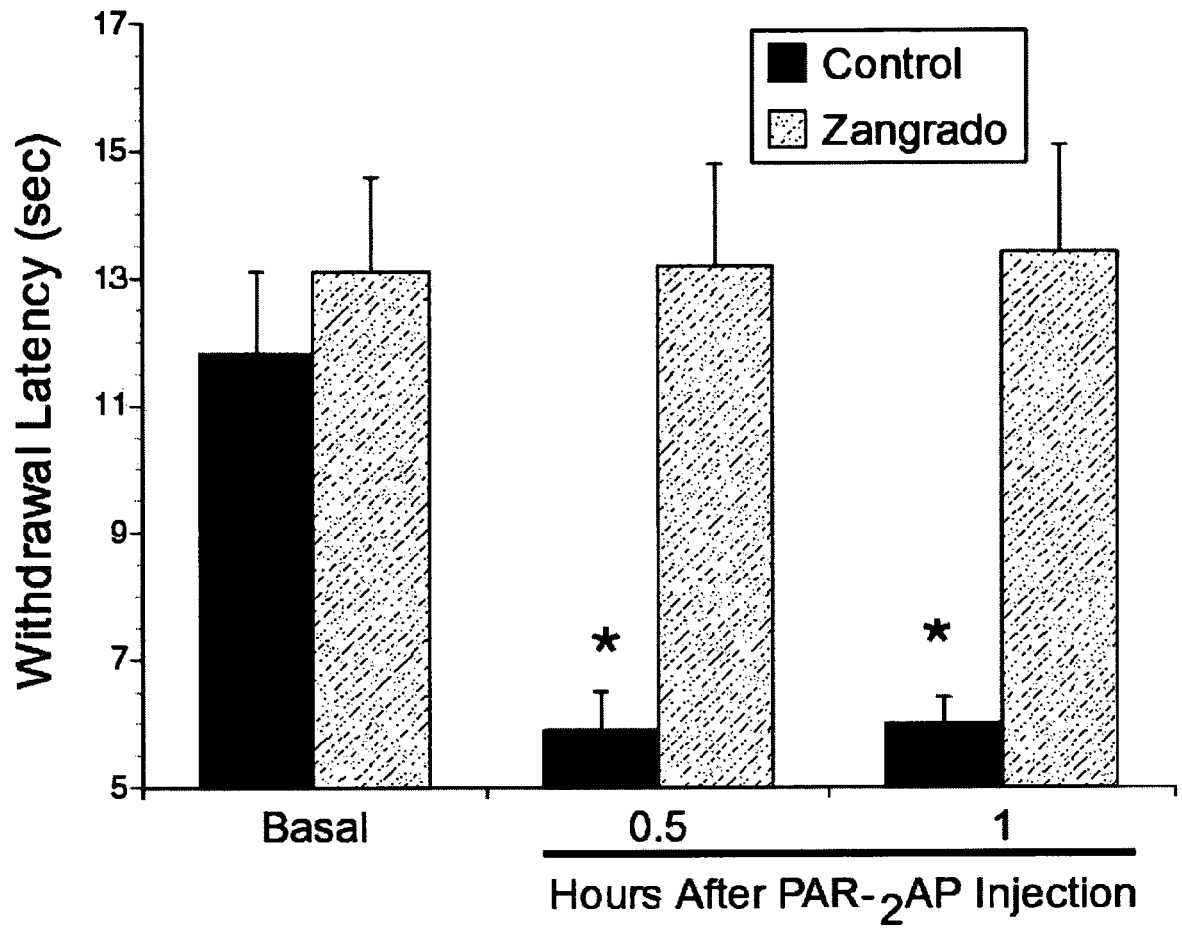
FIG. 4: Using a standard model of pain response, rats were pretreated with Zangrado prior foot pad inoculation with PAR$_2$-AP and subsequent subjection to a thermal stimulus. As determined in a Hargreave's apparatus, pretreatment with Zangrado prevented the induction of hyperalgesia, with the latency withdrawal time remaining at its baseline level despite PAR$_2$-AP administration.

Spraque-Dawley rats (250 g) were anesthetized with sodium pentobarbital. Twenty-two minutes prior to the intradermal injection of protease activated receptor-2 activating peptide (PAR$_{-2}$AP) (SLIGRL-NH$_2$, 50 $\mu$g) into the rat footpad, rats received either 40 mg of placebo balm or a balm containing Zangrado™ (1% Sangre de grado extract) topically to the footpad. Paw withdrawal latency time to a thermal stimulus, as determined in a Hargreave's apparatus, was used as the index of pain sensitivity. Withdrawal times were determined in each group prior to PAR$_2$_AP administration (basal), and then 30 and 60 minutes after administration. A reduction in the latency withdrawal time is used as an index of hyperalgesia, As show in FIG. 4, the intradermal injection of PAR$_2$_AP resulted in a decrease in the latency withdrawal period to a heat source indicative of a state of hyperalgesia. Pretreatment with Zangrado balm 1% prevented the induction of hyperalgesia, with the latency withdrawal time remaining at its baseline level despite PAR$_2$_AP administration. The Zangrado 1% balm did not affect the withdrawal latency in rats that did not receive the PAR$_2$_AP injection (data not shown) indicating that it was not acting as an anesthetic.

Hyperalgesia was also induced by intradermal prostaglandin E$_2$ (PGE$_2$), which is thought to induce an increased sensitivity to pain perception by raising the resting potential of sensory afferent nerve fibers. In these experiments, intradermal PGE$_2$ resulted in a significant reduction in paw withdrawal time and this effect was blocked by a single topical administration of Zangrado 1% balm.

Selective Cytotoxicity of Cancer Cells

While Sangre de grado has traditional uses in the treatment of cancer, its utility is limited because it is equally toxic to both normal and cancerous cells. A process that could retain the ability of Sangre de grado to kill cancer cells but prevented these toxic effects on normal cells would represent a significant improvement over the traditional medicine and a benefit to the treatment of disease in both humans and animals.

To test the selective cytotoxic ability of Zangrado (CGO 110) in vitro, cancerous cells from the gastrointestinal tract (AGS: stomach) and both normal macrophages and normal intestinal epithelial cells (IEC-18) were utilized. Cancerous GI cells were chosen based on Sangre de grado's traditional application for gastrointestinal complications. Cell death was determined by the MTT assay [3-(4,5-dimethylthiazol-2yl)-2,5-diphenyltetrazolium bromide], which assesses cell number by virtue of its oxidative or respiratory activity and the generation of a dye detectable at a wavelength of 550 nm.

Figure 5:
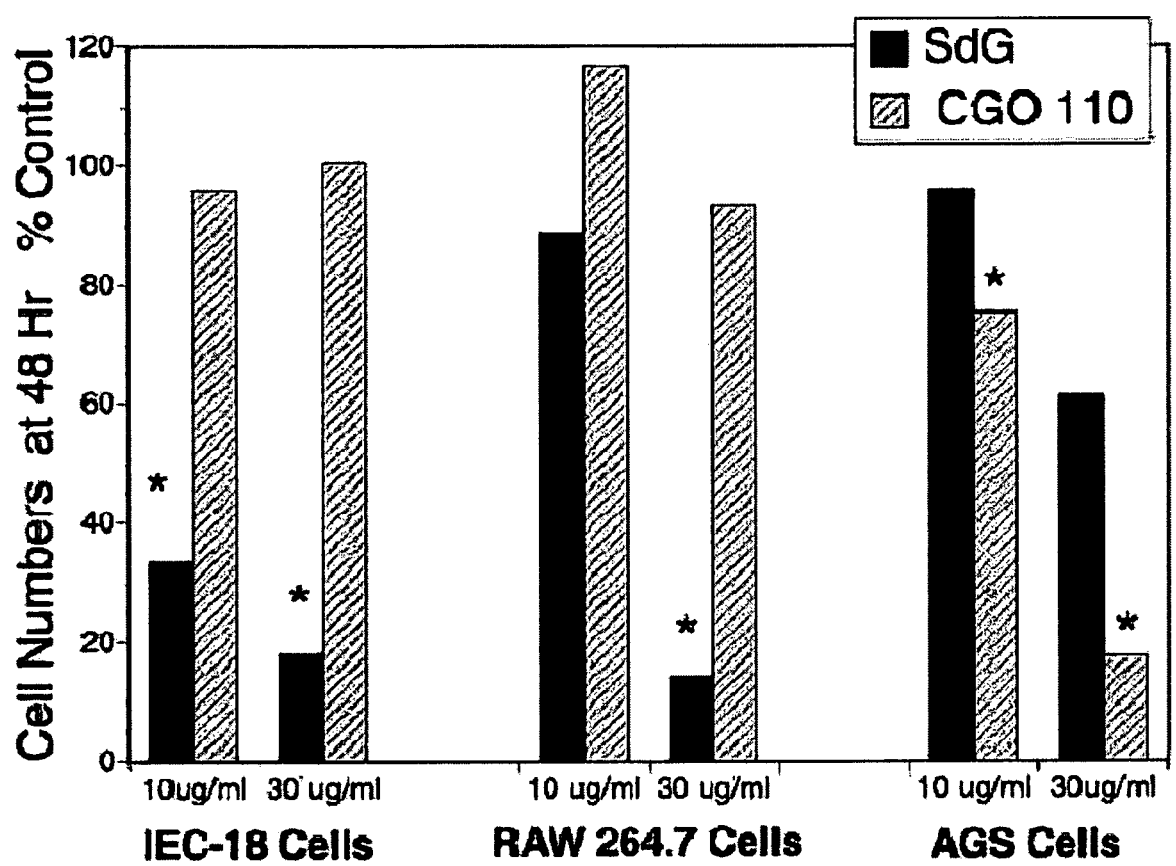
FIG. 5: The selective cytotoxic ability of CGO 110 was tested in vitro in cancerous cells from the gastrointestinal tract (AGS: stomach) and also in both normal macrophages and normal intestinal epithelial cells (IEC-18). In normal cells, Sangre de grado caused significant cell death in both macrophages and IEC-18 cells while the same concentrations of the organic extract CGO 110 did not. In stomach cancer cells (AGS), both CGO 110 and Sangre de grado were cytotoxic and the extract was more potent than the parent botanical. Treatment of stomach cancer cells (AGS) with both CGO 110 and Sangre de grado caused cytotoxicity (cell death), and the lipidic extract, CGO 110, was more potent than the parent botanical [the "*" denotes a significant difference between the Sangre de grado and organic extract CGO 110 formulations ($P<0.05$)]. Collectively, these results indicate that CGO 110 is selectively cytotoxic to cancerous cells compared to the parent botanical, thereby representing a marked improvement in safety.

As shown in FIG. 5, in normal cells, Sangre de grado caused significant cell death in both macrophages and IEC-18 cells while the same concentrations of the organic extract Zangrado (CGO 110) did not. From this we can determine that the lipidic extract Zangrado has improved safety over the parent botanical. Treatment of stomach cancer cells (AGS) with both Zangrado and Sangre de grado caused cytotoxicity (cell death), and Zangrado (CGO 110) was more potent than the parent botanical [the "*" in FIG. 5 denotes a significant difference between the Sangre de grado and organic extract Zangrado (CGO 110) formulations ($P<0.05$)]. Collectively, these results indicate that Zangrado is selectively cytotoxic to cancerous cells compared to the parent botanical, thereby representing a marked improvement in safety.

Reduced Proanthocyandin Content and Color Reactions

Figure 6:
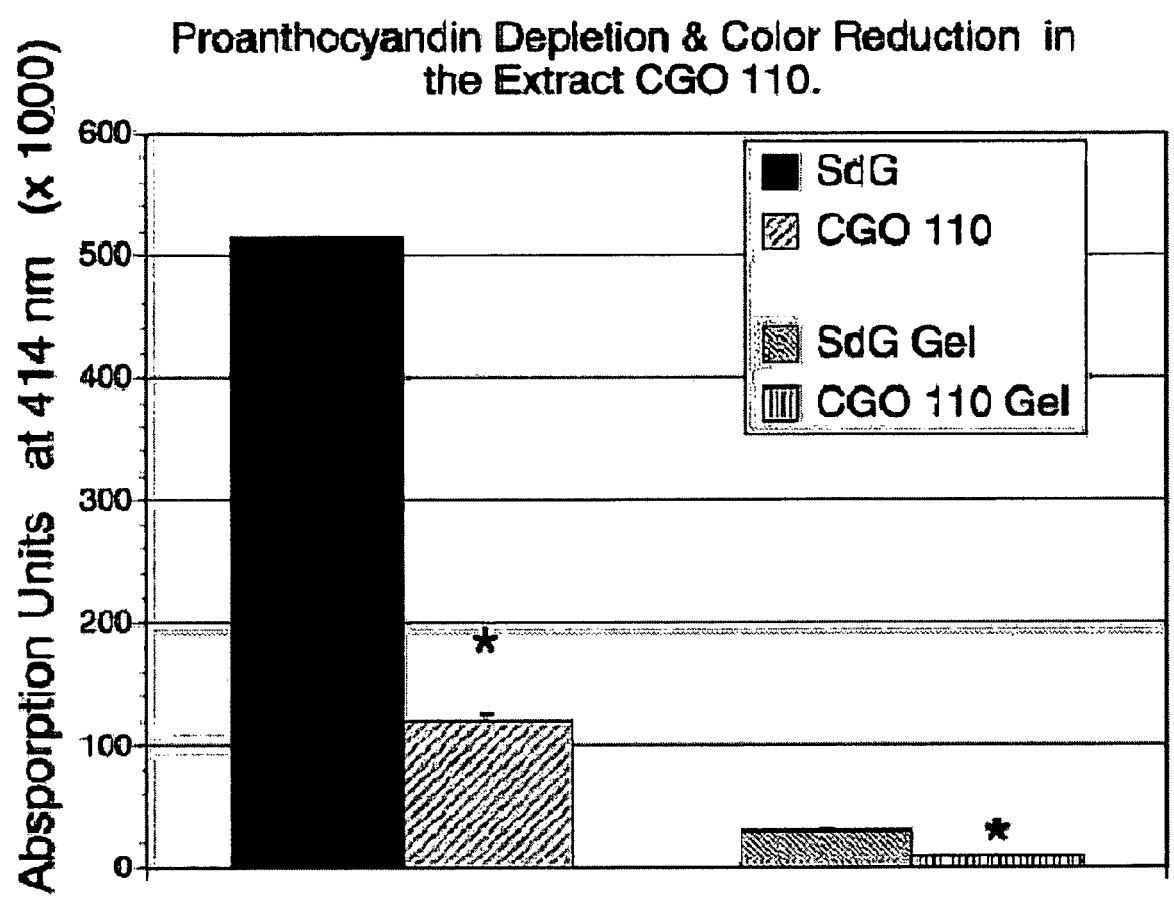
FIG. 6: The extraction process significantly ("*") reduces the proanthocyandin content of the parent latex (SdG). When combined in a base vehicle, such as *Aloe barbadensis* shown here, the extract (CGO 110) produced a mixture absent of the intense color seen in similar preparations with the parent latex. This change, which is readily quantifiable by spectrophotometer, negates the decolorizing (i.e. staining) properties commonly associated with proanthocyandins and the parent latex and allows for practical dermatological preparations.

FIG. 6 illustrates the extent of proanthocyandin depletion accomplished by the extraction processes described herein. Relative absorbency of family Euphorbaciae latex Sangre de Grado (SdG) is compared against a similar quantity of the latex that has been processed according to one of the procedures disclosed herein (Zangrado: CGO 110). As shown in FIG. 6, the extraction processes significantly diminishes the proanthocyandin compounds or content compared to the parent latex material and confirmed by a significant (500%) reduction in absorbency in the 390 to 430 nm range. Since this wavelength range is within the human visible range, the extract Zangrado represents a significant reduction in visible color of this organic extract compared to the parent material.

The presence of the proanthocyandins in the parent latex provides a rich burgundy color to the ethnomedicine, however it also results in the generation of an intense "chocolate" color when combined with various base vehicles, including Aloe barbadensis (aloe vera) gel—and can thus act to stain various materials and textiles. In contrast, the mixture of the organic extract Zangrado (CGO 110) with a similar base vehicle significantly reduces this color reaction, which can be readily quantified spectrophotometrically. FIG. 6 illustrates this result and compares, a similar quantity of aloe barbadensis gel, which has insignificant absorbency in the 390 nm to 430 nm range, mixed with a quantity of the parent latex (SdG Gel), and mixed with a similar quantity of parent latex extracted by a process disclosed herein (CGO 110 Gel).

Sangre de Grado has potential benefits as a topical applicant for various inflamed, itchy and irritated dermatological conditions. However, its inherent color due to high proanthocyandin content and thus the generation of an intense coloring when combined with base vehicles hinders its use for these applications. As the proanthocyandin content and thus coloring are significantly reduced by the disclosed processes, alone or in combination with other topical cremes, gels or base vehicles, Zangrado (CGO 110) signifies a marked improvement in the natural product and its uses.

Absence of Cannabinoid-Induced Hypothermia

Figure 7:
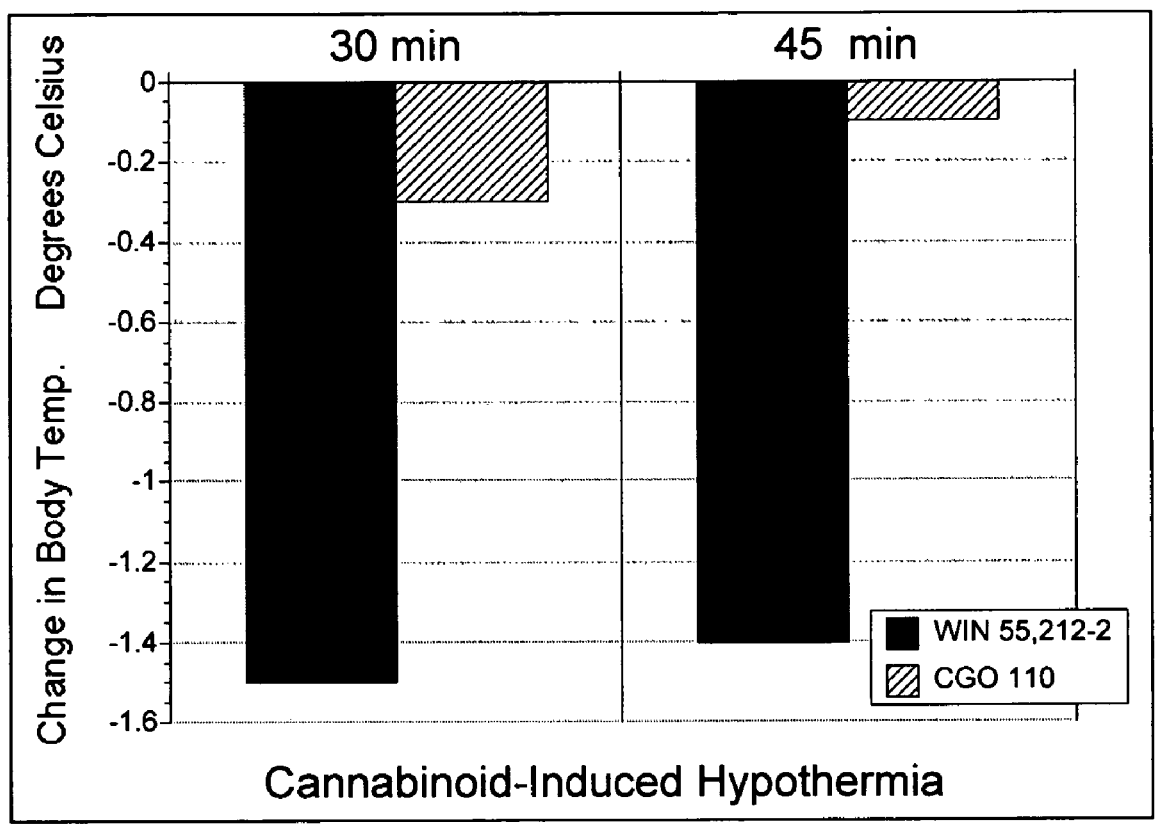
FIG. 7: The cannabinoid agonist WIN 55, 212-2 which like CGO 110 (Zangrado) possesses anti-emetic and anti-itch properties have contrasting effects on body temperature and sedation. The cannabinoid agonist, WIN 55, 212-2 produces a drop in body temperature and significant sedation at anti-emetic doses, whereas CGO 110 (3 mg/kg) does not. This strongly supports the data where cannabinoid antagonists failed to block CGO 110's benefits on itch and emesis, and indicates that CGO 110 does not affect the central nervous system, to elicit undesirable actions and as such represents a significant improvement in the treatment of emesis and itch.

The cannabinoid agonist WIN 55, 212-2 like Zangrado (CGO 110) possesses anti-emetic and anti-itch properties. However, as indicated in FIG. 7, they have contrasting effects on body temperature and sedation. The cannabinoid agonist, WIN 55, 212-2 produces a drop in body temperature and significant sedation at anti-emetic doses, whereas Zangrado (3 mg/kg) does not. This strongly supports the data where cannabinoid antagonists failed to block Zangrado's benefits on itch and emesis, and indicates that Zangrado does not affect the central nervous system and elicit undesirable actions. As such, Zangrado represents a significant improvement in the treatment of emesis and itch.

While the invention has been described with reference to specific preferred embodiments and uses, it is certainly not limited to those precise embodiments or uses. Rather, many modifications, variations and applications will become apparent to persons skilled in the art without departure from the scope and spirit of the invention, as defined in the appended claims.

What is claimed is:

1. A lipophilic extract from family Euphorbaciae, species *Croton* made by a process comprising:
    combining latex from family Euphorbaciae, species *croton* with an organic solvent to produce a combination;
    agitating the combination;
    settling the combination into distinct phases to resolve a layer substantially comprised of hydrophilic constituents and an organic layer substantially comprised of lipophilic constituents;
    separating the organic layer from the layer substantially comprised of hydrophilic constituents;
    adding a drying agent to the organic layer to further precipitate any remaining hydrophilic constituents;
    evaporating the organic solvent from the organic layer to resolve the lipophilic constituents; and
    filtering the organic layer to retain the lipophilic constituents to thereby yield the extract;
    wherein the wavelength absorbency of the extract in a range of 390 nm and 430 nm is reduced by 500% compared to the wavelength absorbency of unextracted latex from family Euphorbaciae, species *croton*.

2. The extract of claim 1 wherein, the organic solvent is selected from the group consisting of ethyl acetate, isopropanol, and chloroform/methanol mixture.

3. The extract of claim 2 wherein, the latex from family Euphorbaciae, species *croton* and the organic solvent are mixed in equal parts.

4. The extract of claim 1, comprising a pharmaceutical dosage that reduces an opiod-induced symptom selected from the group consisting of nausea, emesis, retching and itch.

* * * * *